US00PP13799P29

(12) United States Plant Patent
Smith

(10) Patent No.: US PP13,799 P2
(45) Date of Patent: May 13, 2003

(54) CHRYSANTHEMUM PLANT NAMED 'YOVICTORIA'

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/099,183

(22) Filed: Mar. 15, 2002

(51) Int. Cl.[7] ..... A01H 5/00
(52) U.S. Cl. ..... Plt./291

(58) Field of Search ..... Plt./291

*Primary Examiner*—Bruce R. Campell
*Assistant Examiner*—Annette H. Para
(74) *Attorney, Agent, or Firm*—C. A. Whealy

(57) ABSTRACT

A distinct cultivar of Chrysanthemum plant named 'Yovictoria', characterized by its upright, mounded and rounded plant habit; freely branching habit; dense and full plants; uniform and freely flowering habit; decorative-type inflorescences; light purple-colored ray florets; and natural season flowering in late September in the Northern Hemisphere.

1 Drawing Sheet

BOTANICAL CLASSIFICATION/CULTIVAR DESIGNATION

*Chrysanthemum×morifolium* cultivar Yovictoria.

BACKGROUND OF THE INVENTION

The present invention relates to a new and distinct cultivar of Chrysanthemum plant, botanically known as *Chrysanthemum×morifolium,* commercially known as a garden-type Chrysanthemum and hereinafter referred to by the name 'Yovictoria'.

The new cultivar is a product of a planned breeding program conducted by the Inventor in Salinas, Calif. and Alva, Fla. The objective of the breeding program is to create new garden-type Chrysanthemum cultivars having inflorescences with desirable inflorescence forms, attractive floret colors and good garden performance.

The new Chrysanthemum originated from a cross made in December, 1999, in Salinas, Calif., of a proprietary Chrysanthemum selection identified as code number 97-L092, not patented, as the female, or seed, parent with the Chrysanthemum cultivar Megan, disclosed in U.S. Plant Pat. No. 8,756, as the male, or pollen, parent. The new Chrysanthemum was discovered and selected by the Inventor as a single flowering plant within the progeny of the stated cross grown in a controlled environment in Alva, Fla. in November, 2000. The selection of this plant was based on its desirable inflorescence form, attractive ray floret color and good garden performance.

Asexual reproduction of the new cultivar by terminal cuttings taken in a controlled environment in Alva, Fla. since January, 2001, has shown that the unique features of this new Chrysanthemum are stable and reproduced true to type in successive generations.

SUMMARY OF THE INVENTION

The cultivar Yovictoria has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yovictoria'. These characteristics in combination distinguish 'Yovictoria' as a new and distinct cultivar:

1. Upright, mounded and rounded plant habit.
2. Freely branching habit; dense and full plants.
3. Uniform and freely flowering habit.
4. Decorative-type inflorescences.
5. Light purple-colored ray florets.
6. Natural season flowering in late September in the Northern Hemisphere.

In side-by-side comparisons conducted in Alva, Fla., plants of the new Chrysanthemum differed from plants of the female parent, the selection 97-L092, in the following characteristics:

1. Plant habit of plants of the new Chrysanthemum was more uniform than plant habit of plants of the selection 97-L092.
2. Plants of the new Chrysanthemum flowered more uniformly than plants of the selection 97-L092.
3. Plants of the new Chrysanthemum flowered about one week earlier than plants of the selection 97-L092 when grown under natural season conditions.
4. Plants of the new Chrysanthemum and the selection 97-L092 differed in ray floret color as plants of the selection 97-L092 had orange-colored ray florets.

In side-by-side comparisons conducted in Alva Fla., plants of the new Chrysanthemum differed from plants of the male parent, the cultivar Megan, in the following characteristics:

1. Plants of the new Chrysanthemum had smaller inflorescences than plants of the cultivar Megan.
2. Inflorescences of plants of the new Chrysanthemum did not have conspicuous disc florets whereas inflorescences of plants of the cultivar Megan had conspicuous disc florets.
3. Plants of the new Chrysanthemum flowered more uniformly than plants of the cultivar Megan.

4. Plants of the new Chrysanthemum flowered about five days later than plants of the cultivar Megan when grown under natural season conditions.

Plants of the new Chrysanthemum can be compared to plants of the cultivar Adonis, not patented. In side-by-side comparisons conducted in Alva, Fla., plants of the new Chrysanthemum differed from plants of the cultivar Adonis in the following characteristics:

1. Plants of the new Chrysanthemum flowered more uniformly than plants of the cultivar Adonis.

2. Plants of the new Chrysanthemum had slightly smaller inflorescences than plants of the cultivar Adonis.

3. Flowering of plants of the new Chrysanthemum was not delayed by high production temperatures whereas flowering of plants of the cultivar Adonis was delayed by high production temperatures.

Plants of the new Chrysanthemum can also be compared to plants of the cultivar Padre, not patented. In side-by-side comparisons conducted in Alva, Fla., plants of the new Chrysanthemum differed from plants of the cultivar Padre in the following characteristics:

1. Plants of the new Chrysanthemum had slightly smaller inflorescences than plants of the cultivar Padre.

2. Ray floret color plants of the new Chrysanthemum did not fade as quickly as ray floret color of plants of the cultivar Padre.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Yovictoria'.

The photograph at the bottom of the sheet comprises a close-up view of typical inflorescences of the cultivar 'Yovictoria'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in a fiberglass-covered greenhouse in Alva, Fla. under practices which approximate those generally used in commercial garden-type Chrysanthemum production. One cutting was directly stuck in a 15.25-cm container in November, 2001, and exposed to long day/short night conditions. Plants were pinched once about five weeks after sticking. About one week after the pinch, the photoinductive short day/long night treatments were started. During the production of the plants, day temperatures averaged about 27° C. and night temperatures averaged about 21° C. Measurements and numerical values represent averages for typical flowering plants.

Botanical classification: *Chrysanthemum×morifolium* cultivar Yovictoria.

Commercial classification: Decorative-type garden Chrysanthemum.

Parentage:

*Female, or seed, parent.*—Proprietary selection of *Chrysanthemum×morifolium* identified as code number 97-L092, not patented.

*Male, or pollen, parent.*—*Chrysanthemum×morifolium* cultivar Megan, disclosed in U.S. Plant Pat. No. 8,756.

Propagation:

*Type.*—Terminal tip cuttings.

*Time to initiate roots.*—About four days at 21° C.

*Time to produce a rooted cutting.*—About ten to twelve days at 21° C.

*Root description.*—White, fine and fibrous.

*Rooting habit.*—Freely branching.

Plant description:

*Appearance.*—Perennial herbaceous decorative-type garden Chrysanthemum. Inverted triangle. Stems initially upright, then somewhat outwardly spreading giving a uniformly mounded to rounded appearance to the plant. Freely branching with about five to six lateral branches forming after the pinch.

*Plant height.*—About 18 cm.

*Plant diameter.*—About 26 cm.

*Lateral branches.*—Length: About 14 cm. Diameter: About 3 mm. Internode length: About 1 cm. Aspect: Mostly upright. Texture: Pubescent. Color: 146A.

*Foliage description.*—Leaf arrangement: Alternate. Length: About 5.1 cm. Width: About 4.1 cm. Apex: Cuspidate. Base: Truncate. Margin: Palmately lobed, sinuses mostly divergent. Texture: Both surfaces, pubescent; veins prominent on lower surface. Color: Young and fully expanded foliage, upper surface: 47A. Young and fully expanded foliage, lower surface: 147B. Venation, upper surface: 147A. Venation, lower surface: 147B. Petiole length: About 1.5 cm. Petiole diameter: About 2 mm. Petiole color: Upper surface: 147A. Lower surface: Close to 147B to 147C.

Inflorescence description:

*Appearance.*—Decorative-type inflorescence form with elongated oblong-shaped ray florets. Inflorescences borne on terminals above foliage, arising from leaf axils. Disk and ray florets arranged acropetally on a capitulum. About eleven inflorescences per lateral.

*Flowering response.*—Under natural season conditions, plants flower in late September in the Northern Hemisphere and continue to flower for at least three weeks depending on weather conditions.

*Inflorescence bud (before showing color).*—Height: About 3.5 mm. Diameter: About 5 mm. Shape: Oblate. Phyllary color: 146A to 147A.

*Inflorescence size.*—Diameter: About 4 cm. Depth (height): About 1.9 cm. Disc diameter: About 2 mm, inconspicuous. Receptacle diameter: About 3 mm.

*Ray florets.*—Shape: Elongated oblong. Length: About 1.9 cm. Corolla tube length: About 3.5 mm. Width: About 7.5 mm. Apex: Emarginate. Margin: Entire. Texture: Smooth, glabrous, satiny. Surface: Mostly flat. Orientation: Initially upright, then perpendicular to the peduncle. Number of ray florets per inflorescence: About 95. Color: When opening, upper and lower surfaces: 75A. Opened inflorescence, upper surface: 155D overlain with 75A; overall tonality, 75A to 75B; color fading to 75C to 75D with subsequent development. Opened inflorescence, lower surface: 155D underlain with 75A.

*Disc florets*.—Shape: Tubular, apex dentate. Length: About 4 mm. Width: Apex: About 1.5 mm. Base: About 1 mm. Number of disc florets per inflorescence: Less than 5. Color: Immature: Close to 144A. Mature: Apex: 9A. Mid-section: 150A. Base: 155D.

*Phyllaries*.—Length: About 5 mm. Width: About 2 mm. Shape: Ligulate. Apex: Acute. Base: Truncate. Margin: Entire. Texture: Upper surface, smooth and waxy; lower surface, pubescent. Color, upper surface: 146A. Color, lower surface: 146A to 147A.

*Peduncle*.—Aspect: Flexible, angled about 45° from vertical. Length: First peduncle: About 3.25 cm. Fourth peduncle: About 4.5 cm. Diameter: About 2 mm. Texture: Pubescent. Color: 146A.

*Reproductive organs*.—Androecium: Present on disc florets only. Anther color: 9A to 12A. Pollen: None. Gynoecium: Present on both ray and disc florets. Stigma color: 9A.

*Seed*.—Seed production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to higher than 40° C.

It is claimed:

1. A new and distinct cultivar of Chrysanthemum plant named 'Yovictoria', as illustrated and described.

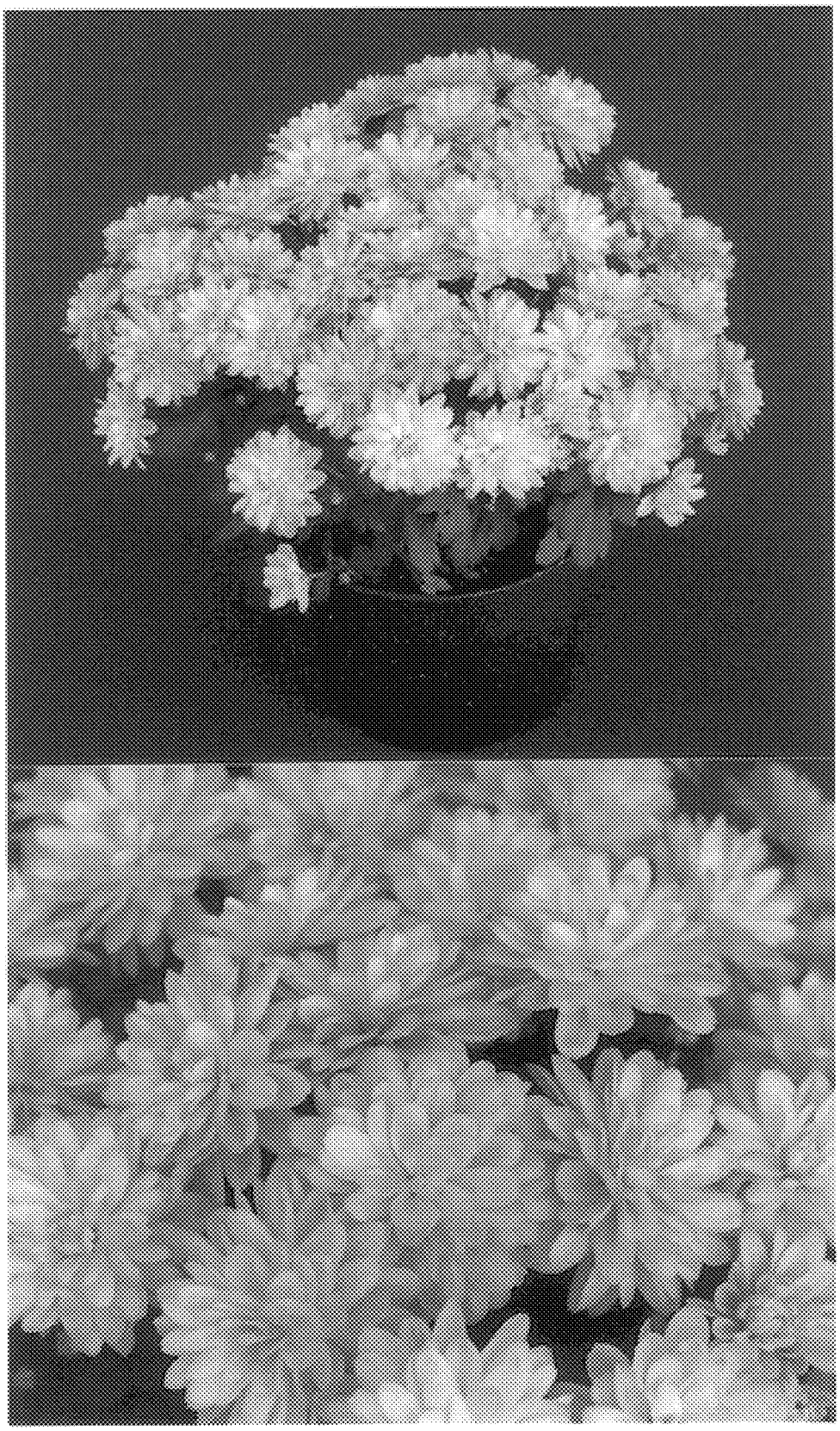

* * * * *